United States Patent [19]
Guskey

[11] Patent Number: 5,965,113
[45] Date of Patent: *Oct. 12, 1999

[54] LOW RESIDUE ANTIPERSPIRANT GEL-SOLID STICK COMPOSITIONS CONTAINING VOLATILE NONPOLAR HYDROCARBON SOLVENTS

[75] Inventor: Gerald John Guskey, Montgomery, Ohio

[73] Assignee: Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/880,940

[22] Filed: Jun. 23, 1997

[51] Int. Cl.$^6$ .............. A61K 7/32; A61K 7/34; A61K 7/38

[52] U.S. Cl. .............. 424/66; 424/65; 424/67; 424/DIG. 5; 514/944

[58] Field of Search ............ 424/65, 66, 67, 424/DIG. 5; 514/944

[56] References Cited

U.S. PATENT DOCUMENTS

| | | | |
|---|---|---|---|
| 4,724,139 | 2/1988 | Palinczar | 424/66 |
| 4,781,917 | 11/1988 | Luebbe et al. | 424/65 |
| 5,429,816 | 7/1995 | Hofrichter et al. | 424/66 |
| 5,591,424 | 1/1997 | Hofrichter et al. | 424/66 |
| 5,650,144 | 7/1997 | Hofrichter et al. | 424/66 |
| 5,744,130 | 4/1998 | Guskey et al. | 424/66 |

FOREIGN PATENT DOCUMENTS

WO 95/30405  11/1995  WIPO.

*Primary Examiner*—Jose'G. Dees
*Assistant Examiner*—Michael A. Williamson
*Attorney, Agent, or Firm*—William J. Winter; Tara M. Rosnell; David L. Suter

[57] ABSTRACT

Disclosed are anhydrous antiperspirant gel-solid sticks which comprise from about 0.5% to about 60% by weight of antiperspirant active; from about 1% to about 15% by weight of a gellant; from about 1% to about 50% by weight of nonpolar volatile hydrocarbon solvent having a solubility parameter of less than 8 $(cal/cm^3)^{0.5}$, a vapor pressure of from about 0.01 mmHg to about 6 mmHg, and an average boiling point of less than about 250° C.; and from about 0.01% to about 10% by weight of a polar, water-miscible solvent having a solubility parameter of from 12.5 $(cal/cm^3)^{0.5}$ to about 25 $(cal/cm^3)^{0.5}$; wherein the composition has a visible residue index of from about 11 to about 30 L-value, a product hardness of from about 500 gram•force to about 5,000 gram•force, and a ratio of an elastic to viscous moduli of from about 0.1 to about 100. These compositions provide improved low residue performance, rheology, efficacy, stability and/or aesthetics from a composition having reduced raw material costs.

30 Claims, No Drawings

LOW RESIDUE ANTIPERSPIRANT GEL-SOLID STICK COMPOSITIONS CONTAINING VOLATILE NONPOLAR HYDROCARBON SOLVENTS

TECHNICAL FIELD

The present invention relates to antiperspirant compositions in the form of gel-solid sticks. In particular, the present invention relates to gel-solid sticks that provide improved low residue performance, efficacy, stability and aesthetics, and which comprise a water-miscible polar solvent and a volatile, nonpolar hydrocarbon solvent.

BACKGROUND OF THE INVENTION

There are many types of topical antiperspirant products that are commercially available or otherwise known in the antiperspirant art. Most of these products are formulated as aerosol or pump sprays, roll-on liquids, creams, emulsions, gels, gel-solids, or other solid stick formulations, and comprise an astringent material, e.g. zirconium or aluminum salts or combinations thereof, incorporated into a suitable carrier. These products are designed to provide effective perspiration and odor control while also being cosmetically acceptable during and after application onto the axillary area or other areas of the skin.

Within this product group, solid anhydrous antiperspirant sticks have become especially popular among consumers. Most of these anhydrous sticks contain up to 80% by weight of a volatile silicone fluid such a cyclomethicone. The volatile silicone provides the composition with improved, drier skin feel during application, and because of its volatility, it quickly evaporates after application leaving the applied surface feeling smooth and dry. Volatile silicones are expensive, however, and add substantially to the cost of the finished product.

One attempt at reducing the cost of anhydrous antiperspirant sticks involves the use of volatile isoparaffins in place of some or all of the volatile silicones. Volatile isoparaffins are typically less expensive than the volatile silicone fluids, and like the volatile silicones, help provide the composition with dry feel during and after application to the skin. Examples of isoparaffin-containing compositions are described in U.S. Pat. No. 4,724,139, issued Feb. 9, 1988 to Palinczar, and U.S. Pat. No. 5,169,626, issued Dec. 8, 1992 to Tanner et al. The compositions described by Palinczar, however, after application to the skin tend to leave a relatively high visible residue, and tend to fracture upon application due to their inherently and relatively high elastic content.

It has now been found that a solid antiperspirant stick composition can be formulated which provides the dry skin feel and low-raw material cost of an isoparaffin-containing antiperspirant, with the low-residue performance and rheology of a gel-solid antiperspirant stick composition. This is accomplished by formulating an anhydrous system with from about 0.5% to about 60% by weight of an antiperspirant active; from about 1% to about 15% by weight of a gellant; from about 1% to about 50% by weight of a volatile nonpolar hydrocarbon solvent having a solubility parameter of less than 8 $(cal/cm^3)^{0.5}$, a vapor pressure of from about 0.01 mmHg to about 6 mmHg at 25° C. under one atomsphere, and an average boiling point of less than about 250° C.; and from about 0.1% to about 10% by weight of polar, water-miscible, solvent having a solubility parameter of from 12.5 $(cal/cm^3)^{0.5}$ to about 25 $(cal/cm^3)^{0.5}$; wherein the composition has a visible residue index of from about 11 to about 30 L-value, a product hardness of from about 500 gram•force to about 5,000 gram force, a ratio of an elastic modulus (G') to a viscous modulus (G") of from about 0.1 to about 100.

It is therefore an object of the present invention to provide an anhydrous antiperspirant gel-solid stick composition which contains volatile, nonpolar hydrocarbon solvents such as volatile isoparaffins, and further to provide such a composition with improved low residue performance, rheology, efficacy, stability and/or aesthetics, and further to provide such a composition having reduced raw material costs.

SUMMARY OF THE INVENTION

The present invention is directed to anhydrous antiperspirant gel-solid stick compositions which comprise from about 0.5% to about 60% by weight of antiperspirant active; from about 1% to about 15% by weight of a gellant; from about 1% to about 50% by weight of nonpolar volatile hydrocarbon solvent having a solubility parameter of less than 8 $(cal/cm^3)^{0.5}$, a vapor pressure of from about 0.01 mmHg to about 6 mmHg at 25° C. and under one atmosphere, and an average boiling point of less than about 250° C.; and from about 0.01% to about 10% by weight of a polar, water-miscible solvent having a solubility parameter of from 12.5 $(cal/cm^3)^{0.5}$ to about 25 $(cal/cm^3)^{0.5}$; wherein the composition has a visible residue index of from about 11 to about 30 L-value, a product hardness of from about 500 gram•force to about 5,000 gram•force, and a ratio of an elastic to viscous moduli of from about 0.1 to about 100.

It has been found that the antiperspirant gel-solid stick compositions of the present invention can provide improved low residue performance, rheology, efficacy, and aesthetics from a composition that contains a volatile, nonpolar, hydrocarbon solvent such as select isoparaffins. It has also been found that these compositions exhibit minimal Ostwald Ripening during prolonged storage thus resulting in improved product stability and reduced solvent syneresis during such prolonged storage.

All of this is accomplished by combining a volatile, nonpolar, hydrocarbon solvent with a water-miscible polar solvent, each having select solubility parameters and other characteristics, and incorporating the combined solvents into the antiperspirant gel-solid stick composition defined herein. The compositions are formulated to have the requisite hardness and rheology profile also defined herein. The requisite hardness and rheology are preferably provided by a non-polymeric, three-dimensional crystalline gel network made up of small, elongated crystalline particles having an average particle size of less than about 1 μm and/or a particle morphology defined by an aspect ratio of greater than about 2.

DETAILED DESCRIPTION OF THE INVENTION

The antiperspirant gel-solid stick compositions of the present invention are anhydrous systems containing antiperspirant active held or contained within a gel-solid matrix. The antiperspirant active can be dissolved or in the form of solid particulates.

The term "anhydrous" as used herein means that the antiperspirant gel-solid stick composition of the present invention, and the essential or optional components thereof other than the antiperspirant active, are substantially free of added or free water. From a formulation standpoint, this means that the antiperspirant gel-solid stick compositions of the present invention preferably contain less than about 5%, more preferably less than about 3%, even more preferably less than about 1%, most preferably zero percent, by weight of free or added water, other than the water of hydration typically associated with the particulate antiperspirant active prior to formulation.

The term "low residue" as used herein refers generally to the visible residue left on the applied areas of the skin during or immediately after application, and more specifically refers to the visible residue index of the composition as defined by the methodology described hereinafter.

The term "ambient conditions" as used herein refers to surrounding conditions under about one atmosphere of pressure, at about 50% relative humidity, and at about 25° C., unless otherwise specified. All values, amounts and measurements described herein are obtained under ambient conditions unless otherwise specified.

The term "substituted" as used herein, unless otherwise specified, refers to chemical moieties or substituents known or otherwise suitable for attachment to the compounds or other chemical materials described or referred to herein. These substituents include, but are not limited to, those listed and described in C. Hansch and A. Leo, *Substituent Constants for Correlation Analysis in Chemistry and Biology* (1979), which listing and description are incorporated herein by reference. Examples of such substituents include, but are not limited to, alkyl, alkenyl, alkoxy, hydroxy, oxo, nitro, amino, aminoalkyl (e.g., aminomethyl, etc.), cyano, halo (e.g., chlorine, fluorine, bromine, iodine), carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, amides, esters, ethers, combinations thereof, and the like.

The term "n-acyl amino acid derivatives" refers to gellants selected from the group consisting of n-acyl amino acid amides, n-acyl amino acid esters prepared from glutamic acid, lysine, glutamine, aspartic acid, and combinations thereof, and which are specifically disclosed in U.S. Pat. No. 5,429,816.

The terms "alkyl" and "alkenyl" as used herein, unless otherwise specified, refer to substituted or unsubstituted, branched, cyclic or linear, hydrocarbons having from 1 to about 22 carbon atoms.

The gellant, antiperspirant active and solvents of the gel-solid stick compositions herein are preferably not refractive index matched, and more preferably have at least two of such components with refractive indices ($\eta_D$) that differ by at least about 0.02.

The antiperspirant gel-solid stick compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Product Characteristics

The antiperspirant gel-solid stick compositions of the present invention are defined in terms of an essential combination of select ingredients and product characteristics, wherein the product characteristics are defined in terms of product hardness, visible residue index, and a rheology profile defined by a ratio of an elastic to viscous moduli. Each of these essential product characteristics is defined hereinafter in detail.

A) Hardness

The antiperspirant gel-solid stick compositions of the present invention have a product hardness of from about 500 gram•force to about 5,000 gram•force, preferably from about 750 gram•force to about 2,000 gram•force, more preferably from about 800 gram•force to about 1,400 gram•force.

The term "product hardness" as used herein is a reflection of how much force is required to move a penetration cone a specified distance and at a controlled rate into an antiperspirant gel-solid stick composition under the following test conditions. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the amount of force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

B) Residue

The antiperspirant gel-solid stick compositions of the present invention have a visible residue index of from 11 to about 30 L-value, preferably from about 11 to about 25 L-value, more preferably from 11 to about 20 L-value. The term "visible residue index" as used herein refers generally to the extent to which the composition of the present invention is visibly apparent as a thin topical film after application to the skin, and more specifically refers to visible residue values (expressed as an L-value on the L, a, b color scale) as measured in accordance with the following methodology, performed at 27° C., under atmospheric pressure, and at 15% relative humidity on antiperspirant stick compositions having a product hardness of from about 500 gram•force to about 5,000 gram•force.

A piece of black felt, approximately 10 cm×30 cm, is attached to a movable horizontal slide which is movably attached or fixed to a larger mechanical unit. An example of a suitable piece of black felt for use herein is Supreme Robe Velour, FN-6554, Color 404L, Style 31854, available from So-Fro Fabrics, Evendale, Ohio, U.S.A. An example of a suitable mechanical assembly for use herein is the Release and Adhesion Tester, Serial No. A-14934, manufactured by Testing Machines, Inc., Amityville, N.Y., U.S.A., or a Velmex Unislide Positioning System, Unislide assembly series (MB6000), available from Velmex, Inc., Bloomfield, N.Y., U.S.A. An antiperspirant stick composition contained within and partially extending out about 0.5 cm from a conventional package or container is positioned perpendicular to and above the attached piece of felt, such that the product extending out of the package or container is facing the piece of felt and the surrounding package is positioned away from the piece of felt. The surrounding package is positioned in place using a mechanical arm or other device suitable for applying the requisite movement to the product as described herein.

The antiperspirant stick composition is then slowly moved toward and allowed to gently contact the attached piece of black felt. A 500 gram weight is placed on the product sample so that the product continuously contacts the piece of black felt during testing. The black piece of felt is then moved repeatedly back and forth across the weighted sample at a fixed speed (about 3 cm/second), and with a fixed amount of applied pressure provided by the weighted product, until the about 1.4 grams of the antiperspirant stick composition is evenly applied over a 5 cm×20 cm area of the piece of black felt. The piece of felt is then carefully removed from the apparatus.

A calibrated Minolta CR-300 chromameter (available from Minolta Corp., Ramsey, N.J., U.S.A.) is then used to measure the L-value (on the L,a,b color scale) of the applied surface area. First, a template is placed on top of the piece of felt to facilitate the Minolta readings. Template dimensions are 5 cm×20 cm. The template has twelve circular openings (2.2 cm diameter) positioned within the template, each opening positioned centrally within adjacent 6.5 $cm^2$ areas of the template surface. The template is positioned over the applied surface area of the piece of felt such that each of the twelve circular openings covers a non-overlapping area of the applied surface. The chromameter's view port is fitted into each of the circular openings and L-value measurements taken. An average L-value is then determined for the twelve measurements (standard deviation of less than about 0.8) which then corresponds to the visible residue index as described herein.

It has been found that there is a correlation between the visible residue index range defined herein and the average particle size of the crystalline gellant particles in the antiperspirant gel-solid stick composition of the present invention. Generally, as the average particle size of crystalline gellant particles in the composition decreases, low residue performance improves. In particular, it has been found that a visible residue index of from about 11 to about 30 L-value correlates with an average crystalline gellant particle size of less than about 1 $\mu$m, and/or a crystalline gellant particle morphology characterized by one dimensional crystalline growth such as that resulting in crystalline filaments, fibers, strings or other elongated particles, wherein the aspect ratio as defined by the major and minor axis of the crystalline particle is greater than about 2, preferably greater than about 6. Conversely, solid compositions containing crystalline gellant particles greater than 1 $\mu$m (average particle diameter) have a visible residue index of greater than 30 L-value. In view of this correlation between visible residue index values and average crystalline particle size or elongated particle morphology, the visible residue index measurement can now be used as an alternative means for establishing average crystalline gellant particle size or crystalline gellant morphology, at least to the extent that such average particle size is less than about 1 $\mu$m.

C) Rheology

The antiperspirant stick compositions of the present invention are gel-solids having the select rheology profile defined herein. This rheology profile is defined herein in terms of the elastic (G') to viscous (G") moduli ratio (G'/G") of the gel-solid stick composition. To provide the requisite rheology, the gel-solid stick compositions must have a G'/G" ratio of from about 0.1 to about 100, preferably from about 0.1 to about 50, more preferably from about 1 to about 20, even more preferably from about 5 to about 20. This ratio represents the extent to which the gel-solid stick compositions herein exhibit solid character and the extent to which the compositions exhibit liquid or fluid character, and specifically refers to the numerical ratio G'/G" as determined by the following methodology.

The elastic modulus is a measurement which correlates with the solid character of the gel-solid stick compositions herein, and the viscous modulus is a measurement which correlates with the fluid or liquid character of the gel-solid stick compositions herein. Measurements for G' and G" for purposes of defining the composition of the present invention are determined under ambient conditions using conventional techniques well known in the formulation arts. For example, a Bohlin Stress-Strain Rheometer, available from Bohlin Reologi, Cranberry, N.J., can be used using a cone (about 1°) and plate configuration. About 1.0 mg of the product is carefully removed for the composition with minimal application of shear force and is then placed between the cone and plate fixtures for measurement of G' and G".

It has been found that the gel-solid stick compositions of the present invention exhibit improved low residue performance when formulated as described herein, wherein the composition has the select G'/G" ratio described hereinabove, especially when the defined rheology is associated with a crystalline gel matrix having a preferred small particle size and/or particle morphology as described herein. These gel-solid stick formulations spread smoothly over the skin, and shear quickly and melt during such spreading to form a thin, low residue film over the applied surface.

In particular, it has been found that the gel-solid stick compositions of the present invention have rheology characteristics that result in improved performance, especially low residue performance. These select gel-solid compositions as defined herein behave as solids prior to application while maintained within a canister or other package, but behave more as liquids or fluids during or immediately after application to the skin. In other words, the solid compositions shear thin during application to the skin, melt or almost melt (except for particulate active which remains unmelted) during the shear thinning application, thus resulting in a thin, low residue, liquid or fluid film on the skin during or immediately after topical application to the skin. The applied film is clear or has very low visible residue, and remains substantially as such over extended periods of time after application.

Essential Ingredients

The antiperspirant gel-solid stick compositions of the present invention, having the above-described product characteristics, are further defined in terms of the select combination of essential ingredients resulting in the product characteristics described hereinbefore. The essential ingredients are antiperspirant active, primary gellant, nonpolar volatile solvent, and polar water-miscible solvent. Each of these essential ingredients is defined hereinafter in detail.

A) Active

The anhydrous antiperspirant gel-solid stick compositions of the present invention comprise antiperspirant active suitable for application to human skin. These actives may be dissolved in the selected solvent, or dispersed throughout the composition as unsolubilized solids. The concentration of antiperspirant active in the composition should be sufficient to provide the desired perspiration wetness and odor control from the antiperspirant gel-solid stick formulation selected.

The antiperspirant gel-solid stick compositions of the present invention preferably comprise antiperspirant active at concentrations of from about 0.5% to about 60%, more preferably from about 5% to about 35%, by weight of the composition. These weight percentages are calculated on an anhydrous metal salt basis exclusive of water and any complexing agents such as glycine, glycine salts, or other complexing agents. The antiperspirant active as formulated in the composition are preferably in the form of dispersed solids having a preferred average particle size or diameter of less than about 100 μm, preferably less than about 50 μm. Also preferred are dispersed solid particulates having an average particle size or diameter of less than about 2 μm, even more preferably from less than about 0.4 μm. It has been found that antiperspirant active particles within the preferred particle size ranges provide lower visible residue performance from the gel-solid compositions herein than other less preferred particle size ranges.

The antiperspirant active for use in the antiperspirant gel-solid stick compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant gel-solid stick compositions include those which conform to the formula:

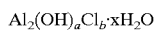

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant gel-solid stick compositions include those which conform to the formula:

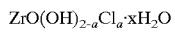

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The antiperspirant gel-solid stick compositions of the present invention can also be formulated to comprise other dispersed solids or other materials in addition to or in place of the antiperspirant active. Such other dispersed solids or other materials include any material known or otherwise suitable for topical application to human skin. The antiperspirant gel-solid stick compositions can also be formulated as gel-solid stick compositions which contain no antiperspirant or other active material, particulate or otherwise.

B) Gellant

The antiperspirant compositions of the present invention comprise a gellant suitable for topical application to human skin. These gellants must form within the composition a crystalline matrix within which the polar and nonpolar solvents or other liquid components of the composition are trapped or contained. These gellants preferably form crystalline particles having an average particle diameter and particle morphology as described herein.

The essential and optional characteristics of suitable gellants for use in the antiperspirant gel-solid stick composition are described in detail herinafter.

1) Gellant description

The concentration of the gellant or gellants in the compositions may vary with each selected antiperspirant gel-solid stick formulation, especially with the selected solvents of the formulation, but such concentrations will generally range from about 0.1% to about 15%, preferably from about 1% to about 12%, more preferably from about 3% to about 12%, by weight of the composition. The gellant must be a solid under ambient conditions.

The gellants for use in the antiperspirant compositions are those which can melt and form a solution or other homogenous liquid or liquid dispersion with the selected solvents, and at the selected gellant and solvent concentrations, at a processing temperature of from about 28° C. to about 250° C., preferably from about 28° C. to about 100° C., more preferably from about 28° C. to about 78° C. The melted gellant is typically dissolved by or dispersed throughout the selected solvents to thus form a solution or other homogenous liquid. The solution or other homogenous liquid, and other essential and optional ingredients, are preferably combined in accordance with the manufacturing method described herein or other conventional or otherwise known technique, and then placed in a suitable package as a flowable solution or homogenous liquid, and then allowed to solidify and form the desired crystalline gel matrix within the composition as the temperature returns to ambient temperature and drops to below the solidification point of the selected gellant.

In selecting a combination of gellant, water-miscible polar solvent and nonpolar volatile solvent for use in the antiperspirant gel-solid stick compositions, the selected combination should allow for the development of a crystalline gellant matrix within the composition wherein the component crystalline particles preferably have an average particle size of less than about 1 μm, more preferably less than about 0.4 μm, even more preferably less than about 0.2 μm, most preferably from about 0.001 μm to about 0.2 μm, and/or wherein the crystalline particles have the requisite elongated morphology described herein, wherein particle size is measured or determined by the methods described herein or by methods well-known to those skilled in the art such as light or electron microscopy. The gel-solid stick compositions can be prepared by methods well known in the formulation art for making gel-solids having minimal crystalline particle size or the preferred elongated particle morphology. The gel-solid stick compositions are preferably prepared by the select methods described hereinafter directed to minimizing crystalline particle size and/or establishing the preferred crystalline particle morphology.

Gellants suitable for use in the antiperspirant compositions of the present invention include fatty acid gellants, esters and amides of fatty acid gellants, hydroxy acids, hydroxy fatty acids, cholesterolic materials, lanolinolic materials, and other amide gellants known for use as gelling agents of which are otherwise described in detail hereinafter. The gellants can be used as a single gellant or as a combination of gellants. Other crystalline gellants can also be used in the antiperspirant compositions of the present invention provided that such other gellants can be formulated to provide the requisite crystalline gel matrix.

Suitable amide gellants include disubstituted or branched monoamide gellants, monosubstituted or branched diamide gellants, triamide gellants, n-acyl amino acid derivatives, and combinations thereof.

Non-limiting examples of suitable secondary amide gellants include select alkyl amides of a di- and/or tri-basic carboxylic acids which conform to the formula:

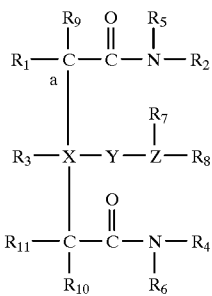

wherein a backbone is formed from the linkage of C', C" and X and wherein a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted aryl, more preferably $C_{12}$–$C_{18}$ alkyl, $C_{12}$–$C_{18}$ alkenyl, $C_{12}$–$C_{18}$ alkoxy, $C_{12}$–$C_{18}$ alkyl esters, $C_{12}$–$C_{18}$ alkyl ethers, or $C_{12}$–$C_{18}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers, preferably a $C_1$–$C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nitrogen, aryl or $-(CH_2)_n-$ where n is an integer from 1 to 6, preferably $-(CH_2)_n-$ where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl; and j) "a" is a double or single bond provided:
  (i) when X and Z are not nil and Y is nil, X is directly bonded to Z;
  (ii) when Z is nil, a hydrogen or a hydroxy, $R_7$ and $R_8$ are nil; and
  (iii) when "a" is a double bond, $R_3$ and $R_9$ are nil.

Some specific examples of suitable alkyl amides of di- and tri-basic carboxylic acids include, but are not limited to, alkyl amides of citric acid, tricarballylic acid, aconitic acid, nitrilotriacetic acid and itaconic acid such as 1,2,3-propane tributylamide, 2-hydroxy-1,2,3-propane tributylamide, 1-propene-1,2,3-trioctylamide, N,N',N"-tri(methyldecylamide)amine, 2-docecyl-N,N'-dibutylsuccinamide, and combinations thereof. Preferred are alkyl amides of di-carboxylic acids, more preferably 2-docecyl-N,N'-dibutylsuccinamide.

Nonlimiting examples of n-acyl amino acid derivatives include n-acyl amino acid esters and n-acyl amino acid amides, specific examples of which include N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutarnic acid ditetradecyl amide, N-stearoyl-glutamic acid dihexadecyl amide, and N-stearoyl-glutamic acid distearyl amide. Preferred are n-lauroyl-glutamic acid dibutyl amide, n-stearoyl-glutamic acid dihexyl amide, and combinations thereof.

The select alkyl amide gellants are preferably synthesized by direct amidation of the corresponding di- or tri-basic organic acid with the appropriate alkyl amine under suitable reaction temperatures, followed by removal of excess amine from the resulting mixture containing the alkylated amide gellants.

The select alkyl amide gellants may also be synthesized by esterification of the corresponding di- or tri-basic organic acid with methanol using a boron trifluoride catalyst followed by removal of the excess methanol and catalyst. The resulting trimethyl ester is then amidated using the appropriate alkylamine followed by removal of excess amine. The resulting alkyl amides for use in the composition should be non-polymeric.

Suitable fatty acid gellants include, but are not limited to, hydroxy fatty acids including alpha-hydroxy acids and 12-hydroxystearic acid and derivatives thereof (including amides and esters thereof), fatty acids having from about 10 to about 40 carbon atoms (e.g., behenic acid, eurcic acid, stearic acid) and related gellants, some preferred examples of which are disclosed in U.S. Pat. No. 5,429,816, issued to Hofrichter et al. on Jul. 4, 1995; and U.S. Pat. No. 5,552,136, issued to Motley on Sep. 3, 1996, disclosures of which are incorporated by reference herein. Preferred are 12-hydroxystearic acid and derivatives thereof.

Preferred antiperspirant compositions are those which comprise a gellant system containing a hydroxy fatty acid gellant as described herein in combination with an n-acyl amino acid derivative as a secondary gellant, wherein the ratio of the hydroxy fatty acid gellant to the secondary gellant is from about 1:2 to about 20:1, preferably from about 2:1 to about 5:1. Most preferred are combinations of n-lauroyl-glutamic acid dibutyl amide and 12-hydroxystearic acid. Examples of these preferred gellant systems are described in U.S. Pat. No. 5,429,816.

2) Preferred primary enantomeric gellants

Preferred gellants for use herein include those enantomeric compounds or materials containing at least one asymmetric (chiral) carbon atom. Non-limiting examples of these preferred enantomeric gellants include 12-hydroxystearic acid, other hydroxy acids such as alpha hydroxy acids, cholesterols, lanolin, and derivatives thereof.

It has been found that these preferred enantomeric gellants, when used in the anhydrous antiperspirant gel-solid stick compositions herein, provide the composition with the requisite product hardness, visible residue index values and rheological properties (G'/G"). It is believed that these enantomeric gellants are especially effective in forming one-dimensional elongated particles in the form of filaments, fibrils or strings which are intertwined or twisted to form a stable, three-dimensional crystalline matrix in the gel-solid composition. These elongated particles have an aspect ratio of greater than about 2, preferably greater than about 6. It is believed that these gellants form elongated crystalline particles that result in a stable crystalline matrix that, in part because of the small size and elongated morphology of these particles, cause less scattering of light when applied to the skin in the antiperspirant composition, which then results in low visible residue after such application.

3) Preferred particle morphology

The gellants for use herein preferably include those crystalline gellants that inherently form, or can be formulated or otherwise made to form, elongated crystalline particles having an aspect ratio greater than about 2, preferably greater than about 6. These elongated crystals preferably have an average particle size as measured along a minor axis of the elongated crystal of less than 1 $\mu$m, more preferably less than about 0.4 $\mu$m, even more preferably less than about 0.2 $\mu$m, most preferably from about 0.2 $\mu$m to about 0.001 $\mu$m.

The antiperspirant compositions containing these preferred elongated crystals can be prepared by methods described herein, or by methods or techniques otherwise known in the formulation art for establishing gel matrices comprising these preferred elongated crystalline particles.

The "aspect ratio" as used herein to define preferred embodiments of the compositions herein can be determined by measuring or otherwise determining the ratio of the length of the major axis of the crystalline particles to the length of the minor axis of the crystalline particles. This length ratio of the major to minor axis is characterized as the aspect ratio referred to herein. The aspect ratio can be determined by conventional or otherwise known light or electron microscopy methods, wherein the crystalline particles are measured for major and minor axis dimensions, or are otherwise observed by such methods to clearly have an apparent elongated crystalline structure with an aspect ratio substantially greater than about 2, preferably greater than about 6.

It has been found that these crystalline gellants having the select aspect ratios defined herein, provide the antiperspirant compositions with a three-dimensional crystalline structure that can provide the composition with low residue performance, and a preferred elastic to viscous moduli ratio and product hardness. It is believed that this crystalline morphology is especially effective in providing a crystalline matrix within the composition that provides for a strong interlocking gel-solid matrix network, but which also comprises crystalline particles that are sufficiently small in size so as to contribute minimally to visible residue when applied topically to the skin.

In particular, it has been found that a visible residue index of from about 11 to about 30 L-value correlates with an average crystalline gellant particle size of less than about 1 $\mu$m, and/or a crystalline gellant particle morphology characterized by one dimensional crystalline growth such as that resulting in crystalline filaments, fibers, strings or other elongated particles, wherein the aspect ratio as defined by the major and minor axis of the crystalline particle is greater than about 2, preferably greater than about 6.

4) Optional dimer-to-monomer ratio

The gellant of the antiperspirant gel-solid stick compositions herein preferably comprise a fatty acid gellant as a primary gellant having a select dimer-to-monomer ratio. The fatty acid gellants having the requisite dimer-to-monomer ratio may be used alone or in combination with an additional or secondary gellant in the composition. The select dimer-to-monomer ratio helps provide the gel-solid stick compositions herein with improved low residue performance, efficacy, stability and aesthetics, and especially provides for improved low residue performance and improved product hardness.

The fatty acid gellants in the antiperspirant gel-solid stick composition, when used in combination with an additional or secondary gellant, has a select dimer-to-monomer ratio of from about 1:1 to about 25:1, preferably from about 1.5:1 to about 25:1, more preferably from about 2.5:1 to about 20:1, even more preferably from about 3:1 to about 10:1. The higher dimer-to-monomer ratios are preferred.

The dimer-to-monomer ratio of the fatty acid gellant can be determined by methods or techniques known in the formulation arts, including infrared methods such as Fourier Transform Infared (FTIR) Spectroscopy. Such methods are disclosed in *The Infared Spectra of Complex Molecules*, L. J. Bellamy, 2nd Edition, 1958, *Introduction to Infared and*

*Raman Spectroscopy*, N. B. Colthup, et. al., 3rd Edition, 1990, and *Fourier Transform Infared Spectroscopy*, P. R. Griffiths, et al., 1986, all disclosures of which are incorporated by reference herein. In accordance with such methods or techniques, fatty acids are usually characterized by their carbonyl stretching frequencies which are measured as absorption bands between 1740 cm$^{-1}$ and 1680 cm$^{-1}$. The fatty acid gellant of the antiperspirant composition of the present invention comprises fatty acid dimers and fatty acid monomers which are components of the carbonyl absorption band. However, due to the formation of hydrogen bonded dimers, the fatty acid dimer component can be shifted as far as 30 cm$^{-1}$ frequencies lower than the fatty acid monomer frequency.

By use of infrared spectra data, the dimer-to-monomer ratio is determined by calculating the ratio of the peak area of the hydrogen bonded dimer second derivative band near 1696 cm$^{-1}$ to the peak area of the fatty acid monomer second derivative band near 1712 cm$^{-1}$. In accordance with the following methodology, an infrared spectra is recorded using a 45° ZnSe Attenuated Total Reflectance ("ATR" herein) crystal and a horizontal ATR apparatus (available from Spectra Tech, Inc., Shelton, Conn., U.S.A.) attached to a Nicolet 20scx FTIR Spectrometer. The Nicolet 20scx FTIR Spectrometer is available from Nicolet Instrument Corporation, Madison, Wis., U.S.A. The Nicolet 205scx FTIR Spectrometer is equipped with a narrow band mercury cadmium Telluride detector whereby an average of 256 scans are co-added to generate the infrared spectra. The infrared spectra is then imported into a computer software program such as GRAMS/386 (available from Galactic Industries Corporation, Salem, N.H., U.S.A.) to calculate the dimer-to-monomer ratio using a 5 point second derivative algorithm which is a mathematical procedure defined by Savitsky-Golay.

The requisite dimer-to-monomer ratio may be established with the fatty acid gellants described herein, which includes alpha-hydroxy fatty acids and fatty acids having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Examples of some suitable fatty acid gellants are described in U.S. Pat. No. 5,429,816, issued to Hofrichter et al. on Jul. 4, 1995; and U.S. Pat. No. 5,552,136, issued to Motley on Sep. 3, 1996, which descriptions are incorporated herein by reference. Most preferred is 12-hydroxystearic acid.

The requisite dimer-to-monomer ratio may also be established with the fatty acid gellants described herein in combination with an additional or secondary gellant, wherein the molar ratio of the fatty acid gellant to the additional or secondary gellant is at least about 0.5:1, preferably at least about 3:1, but typically not more than about 20:1. One of average skill in the chemical or formulation arts can formulate these fatty acid gellant systems to control or otherwise obtain the described ratio.

C) Volatile, Nonpolar, Hydrocarbon Solvent

The gel-solid stick composition of the present invention comprises a volatile, nonpolar hydrocarbon solvent having a select vapor pressure and solubility parameter. Concentration of the volatile, nonpolar hydrocarbon solvent in the gel-solid stick composition ranges from about 1% to about 50%, preferably from about 10% to about 40%, more preferably from 20% to about 40%, even more preferably from about 30% to about 40%, by weight of the composition.

The term "volatile" as used in this context refers to the volatile nonpolar hydrocarbon solvent of the gel-solid stick composition of the present invention, and in this context specifically refers to nonpolar hydrocarbon solvents having a vapor pressure as measured at 25° C. of from about 0.01 mmHg to about 6.0 mmHg, preferably from about 0.02 mmHg to about 2.0 mmHg, and an average boiling point under one atmosphere of pressure (1 atm) of less than about 250° C., preferably less than about 235° C., under 1 atmosphere (atm) of pressure.

The term "nonpolar" as used in this context refers to the volatile nonpolar hydrocarbon solvent of the gel-solid stick composition of the present invention, and in this context specifically refers to volatile solvents having a solubility parameter of less than 8.0 (cal/cm$^3$)$^{0.5}$, preferably from about 5.0 (cal/cm$^3$)$^{0.5}$ to less than 8.0 (cal/cm$^3$)$^{0.5}$, more preferably from 6.0 (cal/cm$^3$)$^{0.5}$ to about 7.60 (cal/cm$^3$)$^{0.5}$.

Solubility parameters for the volatile nonpolar hydrocarbon solvent and other materials described herein are determined by methods well known in the chemical arts for establishing the relative polar character of a solvent or other material. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

Volatile nonpolar hydrocarbon solvents suitable for use in the gel-solid stick compositions are those solvents having the above-described vapor pressure and solubility parameters, which includes hydrocarbons such as some isoparaffins and petroleum distillates having the requisite vapor pressure and solubility parameter. Preferred are nonpolar hydrocarbon solvents which can be cyclic, branched or chain configurations, most preferably branched chain hydrocarbons.

The volatile nonpolar hydrocarbon solvent is most preferably a branched chain hydrocarbon having the requisite vapor pressure and solubility parameter and having from about 4 to about 30 carbon atoms, preferably from about 4 to about 20 carbon atoms, more preferably from about 6 to about 20 carbon atoms. The antiperspirant gel-solid stick composition most preferably comprises a combination of two or more of the above-described branched chain hydrocarbons, wherein the combination of two or more hydrocarbons have different molecular weights, number of carbon atoms, and/or chain configurations. Specific nonlimiting examples of these most preferred combinations of hydrocarbon solvents include the isoparaffins available from Exxon Chemical Company, Baytown, Tex. U.S.A, as Isopar M (C13-C14 Isoparaffin), Isopar C (C7-C8 Isoparaffin), C8-C9 Isoparaffin (Isopar E), Isopar G (C10-11 Isoparaffin), Isopar L (C11-C13 Isoparaffin), Isopar H (C11-C12 Isoparaffin), and combinations thereof. Other nonlimiting examples of suitable branched chain hydrocarbons include Permethyl 99A (isododecane), Permethyl 102A (isoeicosane), Permethyl 101A (isohexadecane), and combinations thereof. The Permethyl series are available from Preperse, Inc., South Plainfield, N.J., U.S.A. Other nonlimiting examples of suitable branched chain hydrocarbons include petroleum distallates such as those available from Phillips Chemical as Soltrol 130, Soltrol 170, and those available from Shell as Shell Sol 70, –71, and –2033.

Nonlimiting examples of other suitable nonpolar, volatile hydrocarbon solvents include, dodecane, octane, decane and combinations thereof, and the Norpar series of paraffins available from Exxon Chemical Company such as Norpar 12, –13, and –15. Yet another example includes C11-C15 alkanes/cycloalkanes, such as those available from Exxon as Exxsol D80.

D) Water Miscible Polar Solvent

The gel-solid stick composition of the present invention comprises one or more water-miscible polar solvents having a selectively high solubility parameter. The concentration of the water-miscible polar solvent in the antiperspirant gel-solid stick composition will vary with the specific combination of water-miscible polar solvent, gellant, volatile nonpolar hydrocarbon solvent, and optional other solvents or gellants in the composition, but should not exceed about 10% by weight of the composition, preferably from about 0.1% to about 5%, more preferably from about 0.1% to about 4%, even more preferably from about 0.1% to about 3%, by weight of the antiperspirant gel-solid stick composition, wherein the water-miscible polar solvent has a solubility parameter of at least 12.5 $(cal/cm^3)^{0.5}$, preferably from 12.5 $(cal/cm^3)^{0.5}$ to about 25 $(cal/cm^3)^{0.5}$, more preferably from 12.5 $(cal/cm^3)^{0.5}$ to about 17.0 $(cal/cm^3)^{0.5}$.

Nonlimiting examples of suitable water-miscible polar solvents for use in the antiperspirant gel-solid stick composition include monohydric alcohols, polyhydric alcohols, and combinations thereof, specific examples of which include, but are not limited to, glycerin, propylene glycol, dipropylene glycol, ethanol, tripropylene glycol, butylene glycol, hexylene glycol, 1,2-hexanediol, propylene carbonate, and combinations thereof. Preferred are propylene glycol, dipropylene glycol, propylene carbonate, glycerin, and combinations thereof. Most preferred is glycerin.

E) Optional Solvents

The anhydrous antiperspirant gel-solid stick compositions of the present invention may further comprise an optional liquid carrier in addition to the polar water-miscible and volatile nonpolar solvents described hereinbefore.

Concentrations of the optional liquid carrier in the gel-solid stick composition will vary primarily with the type and amount of the liquid carrier, the type and amount of the polar water-miscible and volatile nonpolar solvents described hereinbefore, the gellant, and the solubility of the gellant in the optional liquid carrier and other solvents. Preferred concentrations of the combination of solvents and optional liquid carrier in the gel-solid stick composition range from about 10% to about 80%, more preferably from about 10% to about 70%, by weight of the composition.

The optional liquid carrier preferably includes a modified silicone carrier at a concentration ranging from about 0.1% to about 75%, preferably from about 0.1% to about 50%, more preferably from about 1% to about 20%, and even more preferably from about 1% to about 10%, by weight of the antiperspirant gel-solid stick composition.

The optional liquid carrier may include one or more carrier liquids suitable for topical application to human skin, and may include organic or silicone-containing or fluorine-containing, volatile or non-volatile, non-polar or water-miscible polar, solvents or carrier liquids, provided that the resulting combination of optional liquid carrier and other solvents forms a solution or other homogenous liquid or liquid dispersion with the selected gellant at the selected gellant concentration at a temperature of from about 28° C. to about 250° C., preferably from about 28° C. to about 100° C., preferably from about 28° C. to about 78° C.

Optional carrier liquids include modified silicone carriers, provided that such carriers are liquid under ambient conditions, and have a viscosity of less than about 100,000 centistokes, preferably less than about 500 centistokes, more preferably from about I centistoke to about 50 centistokes, and even more preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,084,577, issued to Bolich on Jan. 28, 1992; which descriptions are incorporated herein by reference.

The modified silicone carriers suitable for use in the antiperspirant gel-solid stick compositions include, but are not limited to, compounds or materials as defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu ,e.g. Japanese Patent Publication JP86143760 or from Walker Chem. 6MBH (described in EP722970); alkoxysiloxanes; alkoxysilanes; methicones; and combinations thereof.

Nonlimiting examples of suitable modified silicone carriers for use in the antiperspirant gel-solid stick compositions herein include the following modified silicones available from Dow Coming: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-190 Fluid (Dimethicone Copolyol); DC-193 Fluid (Dimethicone Copolyol); DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cylcomethicone [and] Dimethiconol); DC-8820 Fluid (Amino functionalized); DC Q5-0158A wax (stearoxytrimethylsilane); DC-Q2-8220 (Trimethylsilylamodimethicone); DC-7224 (Trimethylsilylamodimethicone); DC-X2-1318 Fluid (Cyclomethicone [and] Vinyldimethicone); DC-QF1-3593A fluid (Trimethylsiloxysilicate) and combinations thereof.

Other nonlimiting examples of suitable modified silicone carriers for use in the antiperspirant gel-solid stick compositions herein include the following modified silicones available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1328; GE SF-1188 (Dimethicone copolyol); GE SF-1188A (Silicone polyether copolymer); GE SF-1288 (silicone polyether copolymer, dimethyl-methyl 3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsilyl]oxy]trisiloxane); GE SF-1632 (silicone wax); GE SS-4267 (Dimethicone [and] Trimethylsiloxysilicate) and combinations thereof.

Other nonlimiting examples of suitable modified silicone carriers for use in the antiperspirant gel-solid stick compositions herein include the following modified silicones available from Goldschmidt: Abil EM-90 (silicone emulsifier); Abil EM-97 (polyether siloxane); Abil Wax 9810 (silicone wax or C24-28 methicone); Abil Wax 2434 (Stearoxy Dimethicone); Abil Wax 9800D (Stearyl Dimethicone); Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers) and combinations thereof.

Other nonlimiting examples of suitable modified silicone carriers for use in the antiperspirant gel-solid stick compositions herein include the following: Masil 756 from PPG Industries (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Silicone L-711, L-720, L-721 and L722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris [tributoxysiloxy]methylsilane); silicone copolymer F-754 (dimethicone copoly from SWS Silicones); and combinations thereof.

The antiperspirant gel-solid stick composition preferably further comprises a volatile silicone carrier as an optional carrier liquid. These volatile silicone carriers may be cyclic, linear or branched chain silicones having the requisite volatility defined herein. Non-limiting examples of suitable volatile silicones are described in Todd et al., "Volatile Silicone Fluids for Cosmetics", Cosmetics and Toiletries, 91: 27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

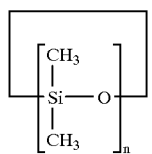

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

The optional liquid carrier may also comprise a non-volatile silicone carrier, preferably in combination with a volatile silicone carrier, and more preferably in combination with a volatile silicone carrier and a modified silicone carrier as described hereinbefore. These non-volatile silicone carriers are preferably linear silicones which include, but are not limited to, those which conform to either of the formulas:

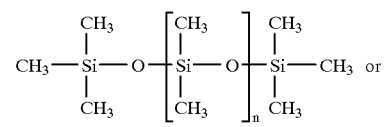

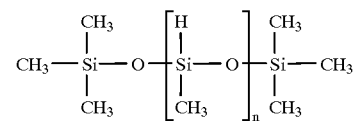

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G. E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

The optional liquid carrier may also comprise other non-polar, nonvolatile, organic carriers such as mineral oil or petrolatum, and any other nonvolatile carrier liquid or solvent known or otherwise safe and effective for topical application to human skin.

The optional liquid carrier may also comprise fluorochemicals such as fluorotelemers and perfluoropolyethers, some examples of which are described in Cosmetics & Toiletries, Using Fluorinated Compounds in Topical Preparations, Vol. 111, pages 47–62, (Oct. 1996) which description is incorporated herein by reference. More specific examples of suitable fluorochemicals include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress® PFPE oils, and the series fluorosurfactants from Dupont Performance Chemicals under the trade name Zonyl® Fluorosurfactants.

F) Optional Nucleating Agent

The antiperspirant gel-solid stick compositions of the present invention may further comprise a nucleating agent for minimizing gellant particle size, and/or for obtaining the preferred gellant particle morphology described herein.

The optional nucleating agent for use in the antiperspirant composition of the present invention must be a solid material under ambient conditions, a solubility in the selected solvents that is less than the solubility of the gellant in the selected solvents, or be in the form of an inorganic, insoluble, micronized particulate. The nucleating agent typically crystallizes, gels, solidifies (except when the nucleating agent is an insoluble, micronized inorganic material), or acts as a nucleus (e.g. promote formation of small gellant nuclei) for the gellant just prior to, just about, or at the same time of crystallization of the gellant in the selected solvents. The molar ratio of the solid gellant to the nucleating agent must be from about 10:1 to about 1000:1, preferably from about 10:1 to about 100:1. These select molar ratios will typically result in nucleating agent concentrations of from about 0.0001% to about 5%, preferably from about 0.001% to about 2%, more preferably from about 0.01% to about 1%. The nucleating agent preferably has a melting point of from about 40° C. below to about 200° C. above, more preferably from about 20° C. below to about 100° C. above the melting point of the selected gellant.

The antiperspirant compositions containing the optional nucleating agent are preferably prepared by 1) combining the gellant, selected solvents and optional nucleating agent as described herein, 2) heating components or the combination of components to form a solution or other homogeneous liquid or liquid dispersion, and 3) solidify the combination of components by cooling the combination to below the solidification point of the solid gellant to form the antiperspirant composition of the present invention.

The nucleating agent for use in the antiperspirant compositions include fatty alcohols, esters of fatty alcohols, ethoxylated fatty alcohols, esters or ethers of fatty acids including waxes, and triglycerides, silica, fumed silica, titanium dioxide, solid polyol carboxylic acid polyesters, and mixtures thereof.

Suitable fatty alcohols for use as optional nucleating agents include monohydric alcohols, ethoxylated fatty alcohols, and fatty alcohol esters. Specific examples of commercially available fatty alcohol nucleating agents include, but are not limited to, Unilin 550, Unilin 700, Unilin 425, Unilin 400, Unilin 350, and Unilin 325, all supplied by Petrolite. Suitable ethoxylated fatty alcohols include, but are not limited, Unithox 325, Unithox 400, and Unithox 450, Unithox 480, Unithox 520, Unithox 550, Unithox 720, Unithox 750, all of which are available from Petrolite. Non-limiting examples of suitable esters of fatty alcohols include tri-isostearyl citrate, ethyleneglycol di-12-hydroxystearate, tristearylcitrate, stearyl octanoate, stearyl heptanoate, trilaurylcitrate.

Suitable fatty acid esters for use as optional nucleating agents include ester waxes, monoglycerides, diglycerides, triglycerides and mixtures thereof. Preferred are the glyceride esters. Non-limiting examples of suitable ester waxes include stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Kester waxes from Koster Keunen, Crodamol SS from Croda and Demalcare SPS from Rhone Poulenc.

Preferred triglyceride nucleating agents include, but are not limited to, tristearin, tribehenate, behenyl palmityl behenyl triglyceride, palmityl stearyl palmityl triglyceride, hydrogenated vegetable oil, hydrogenated rape seed oil, castor wax, fish oils, tripalmiten, Syncrowax HRC and Syncrowax HGL-C (Syncrowax is available from Croda, Inc.). Other suitable glycerides include, but are not limited to, glyceryl stearate and glyceryl distearate.

Preferably the optional nucleating agent is a solid polyol carboxylic acid polyester. Suitable solid polyol carboxylic acid polyesters include those which are polyol esters or polyesters wherein the carboxylic acid ester groups of the polyester comprise a combination of: (a) long chain unsaturated carboxylic acid moieties or a mixture of long chain unsaturated carboxylic acid moieties and short chain saturated carboxylic acid moieties, and (b) long chain saturated carboxylic acid moieties, the ratio of (a) to (b) being from about 1 to 15 to about 2 to 1. At least about 15%, preferably at least about 30%, more preferably at least about 50%, and most preferably at least about 60% by weight of the total carboxylic acid moieties of the polyesters are C20 or higher saturated carboxylic acid moieties. The long chain unsaturated carboxylic acid moieties are typically straight chain and contain at least about 12, preferably about 12 to about 26, more preferably about 18 to about 22 carbon atoms. The most preferred unsaturated carboxylic acids are the C18 mono and/or di unsaturated carboxylic acids. The short chain saturated carboxylic acids are typically unbranched and contain about 2 to about 12, preferably about 6 to about 12, and most preferably about 8 to about 12 carbon atoms. The long chain saturated carboxylic acids are typically straight chain and contain at least about 20, preferably about 20 to about 26, and most preferably about 22 carbon atoms. The molar ratio of Group (a) carboxylic acid moieties to Group (b) carboxylic acid moieties in the polyester molecule is from about 1:15 to about 2:1, preferably about 1:7 to about 5:3, and more preferably about 1:7 to about 3:5. The average degree of esterification of these carboxylic acid esters is such that at least about 2 of the hydroxyl groups of the polyol are esterified. In the case of sucrose polyesters from about 7 to about 8 of the hydroxyl groups of the polyol are preferably esterified. Typically, substantially all, e.g., at least about 85%, preferably at least about 95%, of the hydroxyl groups of the polyol are esterified.

Preferred polyols of the solid polyol carboxylic acid esters are sugars, including monosaccharides and disaccharides and trisaccharides, containing from about 4 to about 11 hydroxyl groups. Most preferred sugars are those which contain about 4 to about 8, more preferably about 6 to about 8 hydroxyl groups. Examples of those containing four hydroxyl groups are the monosaccharides xylose, arabinose, and combinations thereof. Suitable five hydroxyl group-containing polyols are the monosaccharides galactose, fructose, mannose, glucose, and combinations thereof. Examples of disaccharide polyols which can be used include maltose, lactose, sucrose, and combinations thereof, all of which contain eight hydroxyl groups. The preferred polyol is sucrose.

Examples of long chain unsaturated carboxylic acid moieties include, but are not limited to, lauroleate, myristoleate, palmitoleate, oleate, elaidate, erucate, linoleate, linolenate, arachidonate, eicosapentaentoate, and docosahexaenoate. For oxidative stability, the mono- and diunsaturated fatty acid moieties are preferred.

Examples of suitable short chain saturated carboxylic acid moieties include, but are not limited to, acetate, caproate, caprylate, caprate, and laurate.

Examples of suitable long chain saturated carboxylic acid moieties include, but are not limited to, arachidate, behenate, lignocerate, and cerotate.

Of course, the long chain unsaturated carboxylic acid moieties can be used singly or in mixtures with each other or in mixtures with the short chain saturated carboxylic acid moieties, in all proportions. Likewise, the long chain saturated carboxylic acid moieties can be used in combination with each other in all proportions. Mixed carboxylic acid moieties from source oils which contain substantial amounts of the desired unsaturated or saturated acids can be used as the acid moieties to prepare compounds for use as nucleating agents herein. The mixed carboxylic acids from the oils should contain at least about 30%, preferably at least about 50%, and most preferably at least about 80% of the desired unsaturated or saturated acids. For example, rapeseed oil fatty acids or soybean oil fatty acids can be used instead of pure C12–C16 unsaturated fatty acids. Hardened, i.e. hydrogenated, high erucic rapeseed oil fatty acids can be used instead of pure C20–C26 saturated acids, Preferably the C20 and higher acids, or their derivatives, e.g. methyl or other low alkyl esters, are concentrated for example by distillation. The fatty acids from palm kernal oil or coconut oil can be used as a source of C8 to C12 acids, An example of the use of source oils to make solid polyol polyesters for use in the antiperspirant compositions herein is the preparation of solid sucrose polyester, employing the fatty acids of high oleic sunflower oil and substantially completely hydrogenated high erucic rapeseed oil. When sucrose is substantially completely esterified with a 1:3 by weight blend of the methyl esters of the fatty acids of these two oils, the resulting sucrose polyester will have a molar ratio of unsaturated C18 acid radicals to C20 and higher saturated acid radicals of about 1:1 and about 28.6 weight percent of the total fatty acids in the polyester will be C22 fatty acids.

The higher the proportions of the desired unsaturated and saturated acids in the carboxylic acid stocks used in making the solid polyol polyester, the more efficient the ester will be in its ability to function as a nucleating agent.

Examples of solid polyol carboxylic acid polyester nucleating agents for use in the antiperspirant composition herein include, but are not limited to, the octaester of raffimose in which the esterifying carboxylic acid moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterfying carboxylic acid moieties are laurate, linoleate and behenate in a 1:3:4 molar ratio. A preferred material is sucrose polyester in which the degree of esterification is 7–8, and in which the fatty acid moieties are C18 mono- and/or di-unsaturated and behenic, in a molar ratio of unsaturates: behenic of 1:7 to 3:5. A particularly preferred polyol ester nucleating agent is the octaester of sucrose in which there are about 7 behenic fatty acid moieties and about 1 oleic moiety in the molecule.

The solid carboxylic acid polyesters herein can be made according to prior art known methods for preparing polyesters of polyols. See, for example U.S. Pat. No. 5,306,516, to Letton et al., issued Apr. 26, 1994; U.S. Pat. No. 5,306, 515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Suitable inorganic, micronized, non-solubilized nucleating agents for use in the antiperspirant compositions include materials such as silica, titanium dioxide and combinations thereof. These materials contain submicron particles (average particle size generally less than about 1 $\mu$m, preferably less than about 0.2 $\mu$m) which aid in the production of small gellant crystals or particles.

Preferred nucleating agents, and preferred concentrations of the nucleating agents, for use in the antiperspirant compositions include C18 succinic acid (0.1%), 1,9-nonanedioc acid (0.1%), Teflon (0.1%), silica (0.1%), polysiloxane copolymer (2%), sucrose octabehenate (0.5%, 0.75%, 1.0%), Unilin 350 (0.1%), Unilin 550 (0.1%), Unilin 700 (0.1%), trihydroxystearin (0.1%) and combinations thereof.

J) Other Optional Ingredients

The antiperspirant gel-solid stick compositions of the present invention may further comprise one or more other optional components which may modify the physical, chemical or aesthetic characteristics of the compositions or serve as additional "active" components when deposited on the skin. The compositions may also further comprise optional inert ingredients. Many such optional materials are known in the antiperspirant art and may be used in the antiperspirant gel-solid stick compositions herein, provided that such optional materials are compatible with the essential materials described herein, or do not otherwise unduly impair product performance.

Nonlimiting examples of optional materials include active components such as bacteriostats and fungiostats, and "non-active" components such as colorants, emulsifiers, distributing agents, preservatives, surfactants, residue masking agents, process aides such as viscosity modifiers, and wash-off aids. Examples of such optional materials are described in U.S. Pat. No. 4,049,792, Elsnau, issued Sep. 20, 1977; Canadian Patent 1,164,347, Beckmeyer et al., issued Mar. 27, 1984; U.S. Pat. No. 5,019,375, Tanner et al., issued May 28, 1991; and U.S. Pat. No. 5,429,816, Hofrichter et al., issued Jul. 4, 1995; which descriptions are incorporated herein by reference.

Other nonlimiting examples of optional materials include various processing aids, especially chelators such as those described in U.S. Pat. No. 5,516,511, issued to Motley et al. on May 14, 1996, which description is incorporated herein by reference. The concentration of chelators in the composition range from about 0.01% to about 10%, preferably from about 0.05% to about 5%, more preferably from about 0.1% to about 2%, by weight of the composition. Nonlimiting examples of suitable chelators include acetylacetone, ethylene diamine-N,N,N',N'-tetracetic acid (EDTA), nitrilotriacetic acid, oxalate, citric acid, 1,2-diaminocyclohexane-N,N,N',N'-tetraacetic acid, 4,5-dihydroxybenzene-1,3-disulfonic acid, pyrocatechol-3,5-disulfonate, salicylic acid, 5-sulfosalicylic acid, xylenol orange, aurintricarboxylic acid, 2,2'-pyridyl ethylene diamine, glycine, 8-hydroxyquinoline-5-sulfonic acid, lactic acid, 1,10-phenanthroline, pyridine, pyridine-2,6-dicarboxylic acid, 8-quinolinol, succinic acid, tartaric acid, thioglycolic acid, 1,1,1-trifluoro-3,2'thenolyacetone, triethylene tetramine, and combinations thereof. Preferred is EDTA.

The optional chelants can be used in their salt form. Preferred salts include mono and divalent cations and combinations thereof, to provide a total charge of from 0 to about 4. More preferred salts are Na+, K+, Li+, and Mg++, and mixtures thereof, more preferably Na+ and K+ and mixtures thereof. Most preferred is disodium EDTA.

The antiperspirant gel-solid stick compositions may further comprise up to about 5%, typically from about 0.05% to about 4%, by weight of perfumes or fragrances known or otherwise suitable for application to human skin. These perfumes or fragrances can be selected to provide the composition or the applied surface with the desired aroma, or they can be selected to mask malodors associated with human perspiration or the malodor inherently associated with the antiperspirant gel-solid stick composition (hereinafter referred to as odor masking fragrances). Some nonlimiting examples of suitable odor masking fragrances for use in the antiperspirant gel-solid stick composition are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The antiperspirant gel-solid stick compositions of the present invention can also be formulated to comprise other dispersed solids or other materials in addition to or in place of the antiperspirant active. Such other dispersed solids or other materials include any material known or otherwise suitable for topical application to human skin. The antiperspirant gel-solid stick compositions can also be formulated as gel-solid stick compositions which contain no antiperspirant or other active material, particulate or otherwise.

Methods of Manufacture

The antiperspirant gel-solid stick compositions of the present invention may be prepared by any known or otherwise effective technique, suitable for providing an antiperspirant gel-solid stick composition having the requisite crystalline matrix and other product characteristics described herein. Such methods involve formulation of the essential components of the composition to form a gel-solid having the requisite elastic to viscous moduli ratio, product hardness, and visible residue index, wherein the crystalline matrix within the composition comprises elongated gellant crystals having an aspect ratio of greater than about 2, preferably greater than about 6, and an average particle diameter that is minimized (preferably to less than about 1 $\mu$m) through techniques directed to minimizing crystalline particle size in a composition.

Crystalline particle size in the preferred embodiments of the present invention can be determined by techniques well known in the art, which includes light or electron microscopy of the composition, wherein the composition is formulated for analysis purposes without particulate antiperspirant active or other solid particulates. Without such reformulation, it is more difficult to directly determine and distinguish crystalline gellant particle size and morphology from the particle size and morphology contributed from other non-gellant particulates. The reformulated composition is then evaluated by light or electron microscopy or other similar method.

Techniques for preparing the antiperspirant gel-solid stick compositions of the present invention include those methods suitable for formulating compositions containing small gellant crystalline particles. Suitable techniques for minimizing crystalline gellant particle size include the use of nucleating agents, formulation with select carriers or gellants or carrier/gellant combinations, controlling rates of crystallization including controlling formulation, controlling process flow rate, and processing temperatures, and other methods described herein. All such methods should be applied to the formulation to control or minimize gellant crystal particle size, and/or to form the desired elongated crystalline particles, to thus form the desired crystalline matrix of the composition.

Method of Use

The antiperspirant gel-solid stick compositions may be applied topically to the axilla or other area of the skin in an amount effective to treat or reduce perspiration wetness and malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied to the axilla or other area of the skin, one or two times daily, preferably once daily, to achieve effective antiperspirant and malodor control over an extended period.

EXAMPLES

The following non-limiting examples illustrate specific embodiments of the antiperspirant gel-solid stick compositions of the present invention, including methods of manufacture and use.

Each of the exemplified compositions are prepared by combining all of the listed components except the antiperspirant active and other materials such as optional perfumes, optional chelating agents, and optional inorganic particulates. The combined components are heated to about 100° C. with agitation to form a hot liquid, after which all other materials are added to the heated liquid. The heated liquid is allowed to cool with agitation until just before the point of solidification, at which point the cooled, liquid composition is filled into applicator packages and allowed to cool and solidify to the requisite product hardness.

Each of the exemplified compositions comprise a crystalline gel matrix containing crystalline particles having an aspect ratio of greater than about 6, and an average crystalline gellant particle size of less than about 1 $\mu$m. Each of the exemplified compositions also have a visible residue index of between about 11 and about 30 L-value, a product hardness of between about 500 and 5,000 gram•force, and a G'/G" ratio of between about 0.1 and about 100. Each of the exemplified antiperspirant compositions are applied topically to the axilla area of the skin, in accordance with the methods of use described herein, and provide improved low residue performance, efficacy, stability and aesthetics.

All exemplified amounts are weight percents based on the total weight of the antiperspirant gel-solid stick composition, unless otherwise specified.

TABLE 1

| Ingredient | Example 1 | Example 2 | Example 3 | Example 4 | Example 5 |
|---|---|---|---|---|---|
| C13–C14 Isoparaffin | 39.85 | 49.85 | 39.85 | 39.85 | 39.65 |
| Cyclomethicone D5[1] | 12 | — | 15 | 20 | 15 |
| Petrolatum | 11 | 15 | 10 | 10 | 10 |
| 12-hydroxystearic acid | 12 | 7.75 | 7.75 | 7.75 | 7.75 |
| n-lauryl-glutamic acid dibutylamide | — | 2.25 | 2.25 | 2.25 | 2.25 |
| Dipropylene glycol | — | — | — | — | — |
| Dimethicone 350 cs | — | — | — | — | — |
| Glycerin | 0.15 | 0.15 | 0.15 | 0.15 | 0.15 |

TABLE 1-continued

| Ingredient | Example 1 | Example 2 | Example 3 | Example 4 | Example 5 |
|---|---|---|---|---|---|
| Disodium EDTA | — | — | — | — | 0.2 |
| Sucrose polyester[2] | — | — | — | — | — |
| Al Zr trichlorohydrex gly. | 25 | 25 | 25 | 20 | 25 |
| Perfume | — | — | — | — | — |
| Visible residue (L value) | 30 | 27 | 27 | 26 | 27 |
| Hardness (gram force) | 1000 | 1350 | 1300 | 1300 | 1300 |
| G'/G" | 5 | 10 | 10 | 10 | 10 |

[1]Dow Corning 245 Fluid; General Electric SF 1202
[2]Sucrose octaester esterified predominately with behenic acid moieties

TABLE 2

| Ingredient | Example 6 | Example 7 | Example 8 | Example 9 | Example 10 |
|---|---|---|---|---|---|
| C13–C14 Isoparaffin | 39.55 | 29.70 | 19.5 | 26 | 47.85 |
| Cyclomethicone D5[1] | 15 | 20 | 21 | 35 | 12 |
| Petrolatum | 10 | 11.5 | 20 | — | — |
| 12-hydroxystearic acid | 7.75 | 12.0 | 12.0 | 12.0 | 7 |
| n-lauryl-glutamic acid dibutylamide | 2.25 | — | — | — | 2 |
| Dipropylene glycol | — | — | — | 0.5 | — |
| Dimethicone 350 cs | — | — | — | — | 6.0 |
| Glycerin | 0.15 | 0.30 | — | — | 0.15 |
| Disodium EDTA | 0.2 | — | 1.0 | — | — |
| Sucrose polyester[2] | — | 1.5 | 1.5 | 1.5 | — |
| Al Zr trichlorohydrex gly. | 25 | 25 | 25 | 25 | 25 |
| Perfume | 0.1 | — | — | — | — |
| Visible residue (L value) | 28 | 27.5 | 28 | 30 | 30 |
| Hardness (gram force) | 1000 | 1350 | 500 | 650 | 1100 |
| G'/G" | 5 | 10 | 5 | 5 | 10 |

[1]Dow Corning 245 Fluid; General Electric SF 1202
[2]Sucrose octaester esterified predominately with behenic acid moieties

What is claimed is:

1. An anhydrous antiperspirant gel-solid stick composition comprising:
   (a) from about 0.5% to about 60% by weight of antiperspirant active;
   (b) from about 1% to about 15% by weight of a primary gellant;
   (c) from about 1% to about 50% by weight of nonpolar volatile hydrocarbon solvent having a solubility parameter of less than 8 $(cal/cm^3)^{0.5}$, a vapor pressure of from about 0.01 mmHg to about 6 mmHg, and an average boiling point of less than about 250° C.; and
   (d) from about 0.01% to about 10% by weight of a water-miscible, polar solvent having a solubility parameter of from 12.5 $(cal/cm^3)^{0.5}$ to about 25 $(cal/cm^3)^{0.5}$;
wherein the composition has a visible residue index of from about 11 to about 30 L-value, a product hardness of from about 500 gram•force to about 5,000 gram•force, and a ratio of an elastic to viscous moduli of from about 0.1 to about 100.

2. The composition of claim 1 wherein the primary gellant is selected from the group consisting of 12-hydroxystearic acid, esters of 12-hydroxystearic acid, amides of 12-hydroxystearic acid, and combinations thereof.

3. The composition of claim 2 wherein the composition further comprises a secondary gellant selected from the group consisting of n-acyl amino acid amides, n-acyl amino acid esters, and combinations thereof, wherein the weight ratio of the primary gellant to the secondary gellant is from about 1:2 to about 20:1.

4. The composition of claim 3 wherein the secondary gellant is selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide, alkyl amides of citric acid, tricarballylic acid, aconitic acid, nitrilotriacetic acid and itaconic acid such as 1,2,3-propane tributylamide, 2-hydroxy-1,2,3-propane tributylamide, 1-propene-1,2,3-trioctylamide, N,N',N"-tri(methyldecylamide)amine, 2-docecyl-N,N'-dibutylsuccinamide, and combinations thereof.

5. The composition of claim 4 wherein the primary gellant is 12-hydroxystearic acid and the secondary gellant is N-lauroyl-glutamic acid dibutyl amide in a weight ratio of from about 2:1 to about 5:1.

6. The composition of claim 1 wherein the nonpolar, volatile hydrocarbon solvent is a volatile branched chain hydrocarbon having from about 4 to about 40 carbon atoms.

7. The composition of claim 6 wherein the volatile branched chain hydrocarbon has a solubility parameter of from about 5 $(cal/cm^3)^{0.5}$ to less than 8.0 $(cal/cm^3)^{0.5}$ and a vapor pressure of from about 0.02 mmHg to about 2.0 mmHg at 25° C.

8. The composition of claim 7 wherein the composition comprises a combination of two or more volatile branched chain hydrocarbons having different molecular weights, each of which also has from about 6 to about 20 carbon atoms.

9. The composition of claim 8 wherein the volatile branched chain hydrocarbon is selected from the group consisting of C13-C14 Isoparaffin, C7-C8 Isoparaffin, C8-C9 Isoparaffin, C10-11 Isoparaffin, C11-C13 Isoparaffin, C11-C 12 Isoparaffin, and combinations thereof.

10. The composition of claim 6 wherein the water-miscible polar solvent is selected from the group glycerin, propylene glycol, dipropylene glycol, ethanol, tripropylene glycol, butylene glycol, hexylene glycol, 1,2-hexanediol, propylene carbonate, and combinations thereof.

11. The composition of claim 10 wherein the water-miscible polar solvent is glycerin.

12. The composition of claim 1 wherein the composition further comprises an odor masking fragrance.

13. The composition of claim 1 wherein the composition further comprises from about 0.01% to about 10% by weight of a chelating agent.

14. The composition of claim 13 wherein the chelating agent is selected from the group consisting of ethylene diamine-N,N,N',N'-tetracetic acid, salts of ethylene diamine-N,N,N',N'-tetracetic acid, and combinations thereof.

15. The composition of claim 14 wherein the chelating agent is the disodium salt of ethylene diamine-N,N,N',N'-tetracetic acid.

16. The composition of claim 1 wherein the primary gellant are elongated crystalline particles having an aspect ratio of at least about 2.

17. The composition of claim 1 wherein the primary gellant are elongated crystalline particles having an aspect ratio of at least about 6.

18. The composition of claim 1 wherein the composition has a product hardness of from about 800 gram•force to about 1,400 gram•force and a ratio of an elastic to viscous moduli of from about 0.1 to about 50.

19. The composition of claim 1 wherein the composition further comprises a volatile silicone which conforms to the formula:

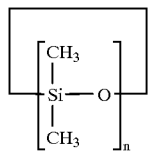

wherein n is from about 3 to about 7.

20. A method for treating or reducing perspiration wetness and malodor, comprising applying from about 0.1 gram to about 20 grams of the composition of claim 1 to the desired area of the skin.

21. An anhydrous antiperspirant gel-solid stick composition comprising:
   (a) from about 0.5% to about 60% by weight of antiperspirant active;
   (b) from about 1% to about 15% by weight of 12-hydroxystearic acid and N-lauroyl-glutamic acid dibutyl amide, wherein the weight ratio 12-hydroxystearic acid to N-lauroyl-glutamic acid dibutyl amide is from about 1:2 to about 20:1;
   (c) from about 1% to about 50% by weight of nonpolar volatile hydrocarbon solvent having a solubility parameter of less than 8 $(cal/cm^3)^{0.5}$, a vapor pressure of from about 0.01 mmHg to about 6 mmHg, and an average boiling point of less than about 250° C.; and
   (d) from about 0.01% to about 10% by weight of a water-miscible, polar solvent having a solubility parameter of from 12.5 $(cal/cm^3)^{0.5}$ to about 25 $(cal/cm^3)^{0.5}$;
wherein the composition has a visible residue index of from about 11 to about 30 L-value, a product hardness of from about 500 gram•force to about 5,000 gram•force, and a ratio of an elastic to viscous moduli of from about 0.1 to about 100.

22. The composition of claim 21 wherein the volatile branched chain hydrocarbon has a solubility parameter of from about 5 $(cal/cm^3)^{0.5}$ to less than 8.0 $(cal/cm^3)^{0.5}$ and a vapor pressure of from about 0.02 mmHg to about 2.0 mmHg at 25° C.

23. The composition of claim 22 wherein the composition comprises a combination of two or more volatile branched chain hydrocarbons having different molecular weights, each of which also has from about 6 to about 20 carbon atoms.

24. The composition of claim 23 wherein the volatile branched chain hydrocarbon is selected from the group consisting of C13-C14 Isoparaffin, C7-C8 Isoparaffin, C8-C9 Isoparaffin, C10-11 Isoparaffin, C11-C13 Isoparaffin, C11-C12 Isoparaffin, and combinations thereof.

25. The composition of claim 6 wherein the water-miscible polar solvent is glycerin.

26. The composition of claim 21 wherein the composition further comprises from about 0.01% to about 10% by weight of the disodium salt of ethylene diamine-N,N,N',N'-tetracetic acid.

27. The composition of claim 21 wherein the primary gellant are elongated crystalline particles having an aspect ratio of at least about 2.

28. The composition of claim 21 wherein the primary gellant are elongated crystalline particles having an aspect ratio of at least about 6.

29. The composition of claim 1 wherein the composition further comprises a volatile silicone which conforms to the formula:

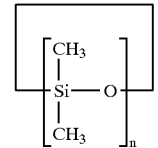

wherein n is from about 3 to about 7.

30. A method for treating or reducing perspiration wetness and malodor, comprising applying from about 0.1 gram to about 20 grams of the composition of claim 21 to the desired area of the skin.

* * * * *